United States Patent
Weinstein

(10) Patent No.: US 7,017,748 B2
(45) Date of Patent: Mar. 28, 2006

(54) SYSTEM AND METHOD TO REDUCE UNCERTAINTY IN PROCURING OVER-THE-COUNTER MEDICATION

(76) Inventor: Robert E. Weinstein, 177 Commonwealth Ave., Boston, MA (US) 02116

( * ) Notice: Subject to any disclaimer, the term of this patent is extended or adjusted under 35 U.S.C. 154(b) by 146 days.

(21) Appl. No.: 10/382,388

(22) Filed: Mar. 6, 2003

(65) Prior Publication Data

US 2004/0140241 A1    Jul. 22, 2004

Related U.S. Application Data

(60) Provisional application No. 60/441,047, filed on Jan. 17, 2003.

(51) Int. Cl.
*B65D 83/04* (2006.01)
(52) U.S. Cl. .................. 206/534; 206/459.5; 705/2
(58) Field of Classification Search ............ 206/534, 206/459.5, 232; 283/70, 81; 215/365; 705/2
See application file for complete search history.

(56) References Cited

U.S. PATENT DOCUMENTS

| | | | | |
|---|---|---|---|---|
| 4,976,351 A | * | 12/1990 | Mangini et al. | 206/232 |
| 5,046,609 A | * | 9/1991 | Mangini et al. | 206/232 |
| 5,797,515 A | * | 8/1998 | Liff et al. | 221/2 |
| 6,036,017 A | * | 3/2000 | Bayliss, IV | 206/534 |
| 6,209,921 B1 | * | 4/2001 | Hogan et al. | 283/70 |
| 6,226,564 B1 | * | 5/2001 | Stuart | 700/231 |
| 6,343,695 B1 | * | 2/2002 | Petrick et al. | 206/534 |
| 6,651,816 B1 | * | 11/2003 | Weinstein | 206/534 |
| 6,843,372 B1 | * | 1/2005 | Weinstein | 206/534 |
| 2002/0184051 A1 | * | 12/2002 | Yu et al. | 705/2 |

OTHER PUBLICATIONS

Lucian L. Leape, MD et al., Systems Analysis of Adverse Drug Events, JAMA, Jul. 5, 1995, pp. 35-43 vol. 274, No. 1.

* cited by examiner

*Primary Examiner*—Bryon P. Gehman
(74) *Attorney, Agent, or Firm*—Robert R. Deleault, Esq.; Mesmer & Deleault, PLLC

(57) ABSTRACT

A system to reduce error in procurement of over-the-counter drugs that has a prescription drug dispensing container that contains a prescription drug, an over-the-counter drug dispensing container that contains an over-the-counter drug, and indicia displayed on the prescription drug dispensing container and the over-the-counter drug dispensing container to link the prescription drug and the over-the-counter drug and thereby guide the procurement of the over-the-counter drug.

10 Claims, 3 Drawing Sheets

SYSTEM AND METHOD TO REDUCE UNCERTAINTY IN PROCURING OVER-THE-COUNTER MEDICATION

This application claims the benefit of U.S. Provisional Application No. 60/441,047 filed Jan. 17, 2003.

BACKGROUND OF THE INVENTION

1. Field of the Invention

The present invention relates generally to drug packaging. Particularly, the present invention relates to drug packaging systems and methods to reduce adverse drug events.

2. Description of the Prior Art

The manufacture and distribution of human drugs in the United States is regulated by the Food and Drug Administration (FDA). The FDA is charged with assessing all drugs for safety and efficacy and is also responsible for determining whether individual drugs are best distributed by prescription or over-the-counter. Prescription drugs, because of toxicity or other potentiality for harmful effect, or the method of its use, or the collateral measures necessary to its use, are considered by the FDA as being not safe for use except under the supervision of a practitioner licensed by law to administer such drug. Over-the-counter drugs are drugs that the FDA has considered to have a limited potential for harmful effect sufficient to allow dispensing directly to lay users without the requirement of licensed practitioner supervision.

The FDA prohibits the sale or representation of a prescription drug other than by prescription, and the sale or representation of an over-the-counter drug other than by over-the-counter. A prescription drug is required, at minimum, to bear the symbol "RX only", and is considered misbranded if at any time prior to dispensing its label fails to bear this. An over-the-counter drug is deemed misbranded if at any time prior to dispensing its label bears a prescription symbol. (The statutory authority for the FDA comes from the Federal Food, Drug and Cosmetic Act (the FDCA, 21 U.S.C. 301 et seq.) and this ruling is found in SEC. 503 (b)(4)).

Although administration under the supervision of a licensed practitioner is not required for over-the-counter drugs, FDA regulations do not prohibit practitioners from "prescribing" or recommending over-the-counter drugs to their patients. The terms "prescribe" and "recommend" in reference to over-the-counter drugs, are herein used synonymously. The recommending of over-the-counter drugs by a caregiver may be accomplished verbally or in writing, including writing on an ordinary prescription blank although not filled by the pharmacist in the manner of a prescription drug.

Despite the FDA efforts to regulate the dispensing of drugs, errors in the dispensing of drugs and consequent adverse effects are known to occur even in the most carefully supervised medical environments. For example, in a front page article entitled "Controls were urged before '95 overdose" on Jul. 12, 1996, the Boston Globe reported "a number of adverse events" including the death of a 67 year old patient due to potassium chloride overdose at Boston's Brigham and Woman's Hospital. It was noted that in the previous year Dr. David Bates published a research paper documenting how medications caused injuries to one of every 15 patients admitted to Brigham and Woman's, and Massachusetts General Hospitals over a six-month period. A Brigham and Woman's hospital committee came to recognize that if the hospital pharmacy were to only stock packaged, premixed solutions of potassium chloride, and not stock the current vials of concentrated potassium chloride, this would markedly reduce the chance of a future occurrence. Such a measure to prevent adverse effects can be referred to as a "system change" in the dispensing of the drug.

The extent of such problems is not limited. Three years later, on Nov. 30, 1999 both the Wall Street Journal and USA Today reported study findings of the Institute of Medicine, a private organization established by Congress to provide advice on medical issues. The study found that between 44,000 and 98,000 Americans die each year as a result of medical mistakes made while they are in the hospital, killing more Americans than traffic accidents, breast cancer or AIDS. Deaths were again noted to result from the stocking of drugs that should not be administered to patients unless they are diluted. The report took notice of "systemic flaws that . . . build the opportunity for error into medical practice." A member of the Institute of Medicine committee, Dr. Lucien Leape of the Harvard School of Public Health, called for the nation's health care system to focus upon its systems rather than mistakes of individual caregivers.

In the article "Systems analysis of adverse drug events," (JAMA 1995; 274: 35–43), Dr Leape, et al. reports that "errors in drug use are common, costly and often result in injury." Further, that ". . . traditional efforts at error reduction have focused on individuals and episodes, using training, exhortation, rules and sanctions to improve performance. Human factors specialists and error experts reject this approach, noting that it is more effective to change the system as a whole to reduce the likelihood of accidents." "Poor system design creates 'accidents waiting to happen'." To enhance safety by design, one would want to create a system "to make it difficulty for individuals to err."

Over-the-counter drugs are generally considered as safe, but this may be misleading. Over-the-counter drugs are not risk-free. Unanticipated and serious adverse effects from unsupervised use of such common medications such as aspirin (peptic ulcer, intractable asthma) and first-generation antihistamines (industrial and motor vehicle injuries caused by impaired cognition) are well known. Some over-the-counter medications have proven to be clearly unsafe and have been removed because of their hazards. The taking of over-the-counter drugs together, or together with prescription drugs opens the door to unintended redundancy, overdose, and drug interactions.

When a caregiver prescribes a prescription drug to be filled by a pharmacy, the caregiver and patient can be reasonably certain that the patient will obtain the correct drug because of the continuous chain of supervision provided by the prescription-dispensing process. When a caregiver recommends an over-the-counter drug to a patient to be obtained at a pharmacy, the present system by which the FDA allows over-the-counter drugs only to be dispensed in that manner places the burden of correctly obtaining the recommended over-the-counter drug upon the patient. Lacking a continuous chain of professional supervision, there is considerably less certainty that the patient will obtain the correct drug.

For at least the following reasons, the procurement of over-the-counter drugs by lay persons can be considered a system that "creates accidents waiting to happen:"

1. The over-the-counter shelf is confusing. This is common knowledge, and can be validated by observing individuals attempting to select a cold remedy and having to differentiate between a myriad of products containing different ingredients in various proportions, each ingredient having its own therapeutic and side effects, and each formulation requiring different dosing timing. It is a certainty that individuals make inappropriate choices in selecting cold medications that, at least, result in unanticipated stimulation or unwanted sedation. Industrial accidents, motor vehicle accidents and aeronautical errors have been documented to be caused by these medications.

2. The ability to navigate the over-the-counter drug procurement process may be even more confusing for limited or impaired individuals.

3. The brand recommended by the physician may not be carried by the particular pharmacy used by the patient. If the patient does not find the particular over-the-counter recommended by the caregiver at his or her pharmacy, the patient may attempt to select a product that appears the same, or possibly forego treatment. Alternatively, the patient may seek the advice of a pharmacist. In the United States at present, the advisory services of pharmacists are not uniformly available to patients seeking help. It is often the case for pharmacists to be rushed and fully engaged in filling prescriptions. Even if assistance were fully available, however, the pharmacist would not have the caregiver's comprehensive knowledge of the patients' medical status and full understanding of the rationale for the caregiver's selection of medication.

4. A branded name may encompass many formulations. As with other retail commodities, over-the-counter drugs compete with each other at the retail shelf. Drug companies frequently develop multiple drug variations under the same brand name and can command increased shelf space in this manner. As an example, a patient suffering with acute sinusitis who is advised by his or her caregiver to procure "Afrin Nasal Spray®" might find one or more of: "Original", "Extra Moisturizing", "Severe Congestion", "Allergy", "Sinus", or "Saline Mist" varieties upon reaching the pharmacy. If the "Afrin®" brand is not stocked, the patient might find another brand such as "Neo-Synepherin®", but then have to deduce the utility of "Regular Strength", "Extra Strength", "Mild Formula", and "Extra Moisturizing" preparations. Among these formulations are some with one decongestant, some with another decongestant, and some that have no decongestant at all.

5. The formulation of an over-the-counter product may change from time to time. It has been estimated that there are over 100,000 non-prescription over-the-counter products and changes can easily escape the caregiver's scrutiny and usually occur without notification to caregivers.

Therefore, what is needed is drug system and method that utilizes prescription and over-the-counter drugs in a coordinated system together to minimize error in patient procurement of over-the-counter medications. What is further needed is a drug system and method that provides greater control of the over-the-counter medications that the caregivers intend for their patients. What is also needed is a drug system and method that reduces the confusion and uncertainty created by the myriad of over-the-counter products from which a patient must differentiate.

SUMMARY OF THE INVENTION

It is an object of the present invention to provide a drug system and method to improve treatments that utilize prescription and over-the-counter drugs together and particularly to minimize error in the procurement of over-the-counter medications by patients in this situation. It is another object of the present invention to afford caregivers increased control of the over-the-counter medications that they intend their patient to receive. It is a further object of the present invention to overcome the confusion and uncertainty created by the myriad of over-the-counter products from which a lay user has to differentiate. It is still another object of the present invention to provide prescription drug and over-the-counter medication in packaging such that the dispensing packaging of the prescription drug may be linked to the dispensing packaging of the over-the-counter drug by indicia that serves to guide a user to procure the over-the-counter drug.

The present invention achieves these and other objectives by providing a prescription product in a dispensing package that has guiding indicia and an over-the-counter drug in a dispensing package with the same or complementary indicia that is confirmatory. The present invention is based upon the insight that when a combination of medications, one obligatorily dispensed by prescription and another obligatorily dispensed over-the-counter, are the intended treatment of a caregiver, the prescription drug process can be harnessed to improve the certainty of the patients procuring the intended over-the-counter drug. The present invention links the procurement of the over-the-counter drug to the more certainly dispensed RX drug makes it more difficult for individuals to err in choosing the over-the-counter medication. The present invention also affords the caregiver improved control and the patient increased assurance of receiving the intended treatment.

The prescription drug is prepackaged in a dispensing container having indicia that serves to guide the patient to select a particular over-the-counter drug. The complementary over-the-counter drug is also prepackaged in a dispensing container having indicia on its surface that confirms the selection by the patient of the proper over-the-counter drug.

DETAILED DESCRIPTION OF THE PREFERRED EMBODIMENT

Figure 1:
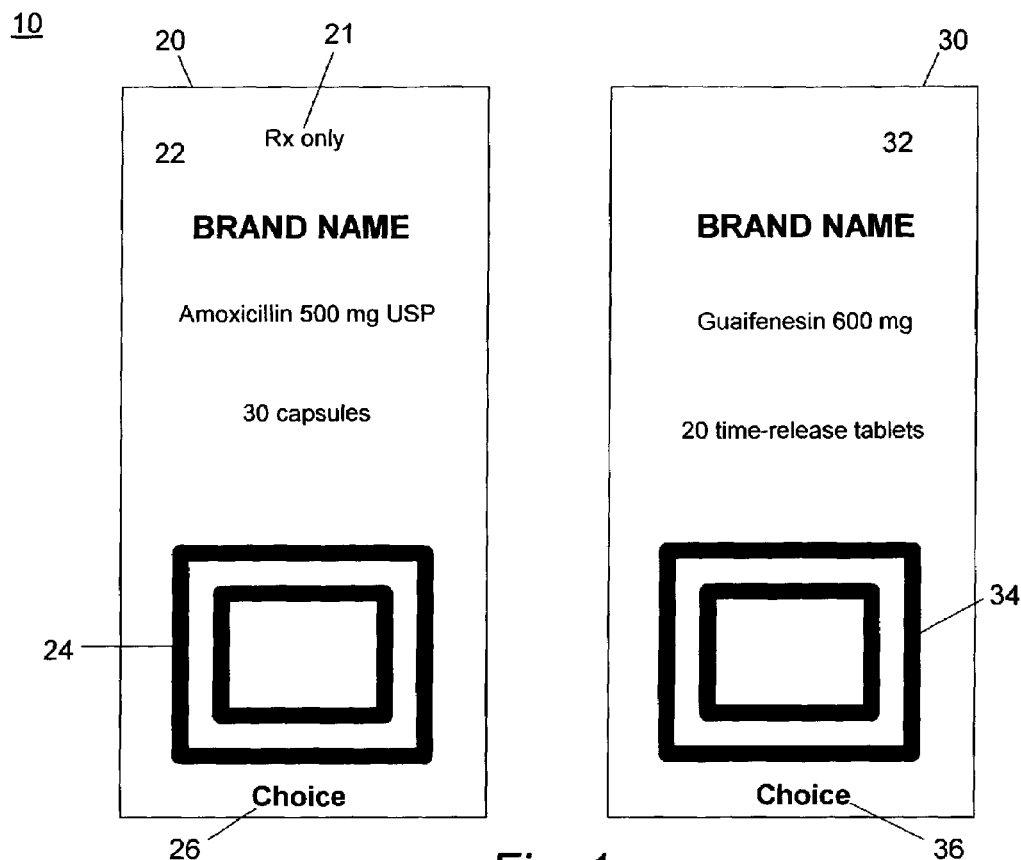
FIG. 1 is a front plan view of one embodiment of the present invention.

The preferred embodiment(s) of the present invention are illustrated in FIGS. 1–4. FIG. 1 illustrates front planar views of the drug packaging system 10. Drug packaging system 10 includes a prescription drug dispensing container 20 and an over-the-counter drug dispensing container 30. Prescription drug dispensing container 20 includes a symbol 21 ("Rx only") and a linking indicia 24 on front surface 22. Over-the-counter dispensing container 30 purposely does not have the "Rx only" symbol but includes a complementary linking indicia 34 on front surface 32. Both linking indicia 24 and 34 are identical indicating linkage or commonality. Linking indicia 24 and 34 may be any symbol or shape such as, for example, a double rectangle. Both dispensing containers 20 and 30 may have additional linking indicia 26 and 36, respectively. In this embodiment, the word "Choice" is used as the additional linking indicia 26 and 36 to also indicate commonality and excluding medications that do not have this word or name on them. In this example, it is intended that either or both linking indicia 24 or 26 on the prescription drug container 20 serve as a guide for the patient to select and procure the over-the-counter drug with the same linking indicia. Indicia 34 and 36 on the over-the-counter drugs serve to match the prescription drug linking indicia 24 and 26, and confirm to the patient that he or she has selected the intended drug. It is appreciated that two different drugs cannot be given the same drug name. It is also to be understood that as well as the illustrated symbols and words, the prescription drug and over-the-counter dispensing packages 20 and 30 might be linked by colors, package shapes, design, and other indicia, and that such indicia are within the scope of the present invention. It is important that the indicia be prominent on the packaging and that it not be a manufacturer's name or drug brand name in order to reduce the potential for confusion and error in selecting the proper package.

In the example shown in FIG. 1, the prescription is an antibiotic and the over-the-counter drug is an expectorant. Prescription drug dispensing container 20 is depicted to contain thirty amoxicillin 500 mg capsules and the over-the-counter container 30 is depicted to contain twenty time-release guaifenesin 600 mg tablets. Caregivers might recommend such a combination of drugs, for example, as a regimen to treat sinusitis or upper respiratory tract infection. In the event that the caregiver were to intend to treat a patient with these particular drugs, the caregiver would conventionally prescribe the prescription drug and advise the patient to procure the over-the-counter drug, preferably in writing, or verbally as is commonly done. Caregivers are well aware of the potential for error and mishap when recommending an over-the-counter drug to a patient and describing the product to be procured to the patient. The present invention represents a tool, heretofore unavailable, that allows a caregiver to reduce the potential for error. Because it is strongly in the caregiver's interest to avoid error and mishap, it can be expected for caregivers to advise patients to use the linking indicia as a "red flag" to positively identify the intended product and thereby reduce the risk of inadvertent procurement of unintended medication. One advantage of the present invention over written caregiver instructions or descriptions, which can be lost, is that the guiding and confirming indicia on the dispensing containers are always present and reminding at the very time of procurement.

Even though the present invention would require the pharmacy to stock both the prescription drug and over-the-counter items in to fulfill its intended purpose, drug packaging system 10 provides many advantages for the pharmacy. It is common for pharmacists to be required to fill containers with prescription medication prior to dispensing. Drugs using packaging system 10 of the present invention are pre-packaged by a manufacturer in an amount intended for procurement by a user. This "unit-of-use" prescription drug packaging has the advantage of eliminating the container-filling step by the pharmacist, saving time and cost, and, importantly, eliminating the potential for error associated with prescription drugs that ordinarily require filling. For conveying the intended over-the-counter drug to a patient, little else is required of the pharmacist other than possibly pointing out the indicia on the prescription drug dispensing container to the patient and/or pointing to the shelf where the patient can pick up the over-the-counter drug in the linking container. The pharmacist is neither burdened in instances when the caregiver has chosen to recommend the over-the-counter drug on a prescription sheet or when the caregiver has given verbal, or preferably written, instruction directly to the patient.

Drugs in the form of pills, tablets, capsules and the like are well known in the art to be prepackaged by manufacturers for users in sealed formats such as bottles or blisters. The devising and manufacture of prepackaged prescription and over-the-counter drugs in the manner the drug packaging system 10 of the present invention requires expertise at least commensurate with that of a pharmaceutical manufacturer. The manufacturer has considerable control over the system and it is obligatory that the manufacturer does not manufacture additional drugs in dispensing containers with the same or similar indicia that would cause confusion.

Figure 2:
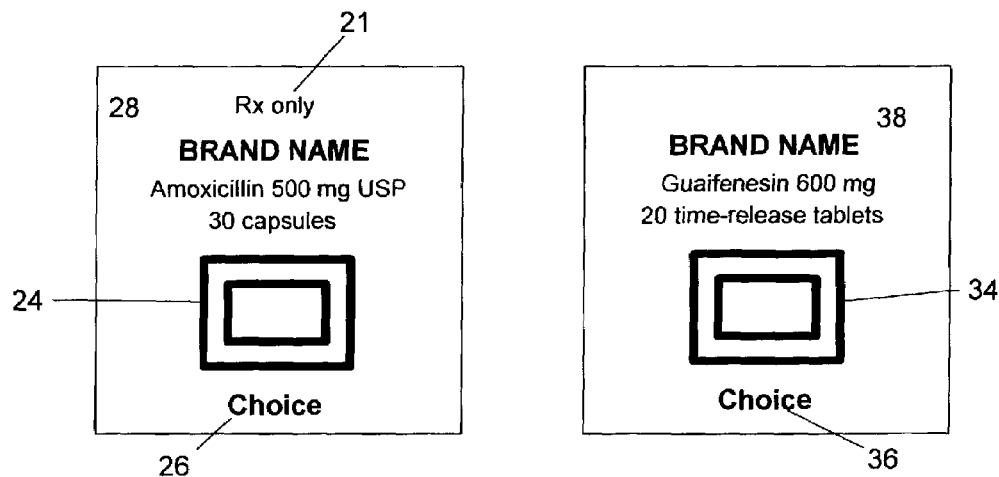
FIG. 2 is a top plan view of the embodiment of the present invention in FIG. 1.

FIG. 2 depicts top planar views of the prescription and over-the-counter drug dispensing containers 20 and 30. In this example, linking indicia 24, 34 and 26, 36 are reiterated on the top surfaces 28 and 38 of containers 20 and 30, respectively. Symbol 21 (Rx only) is also reiterated on top surface 28. Because information on dispensing boxes can become obscured with stickers such as pricing or other labels applied by pharmacies, this example is given to illustrate a preference for the repetition of both guiding and confirming indicia on dispensing containers 20 and 30. It should be understood that guiding and confirming indicia may be placed on various surfaces of the drug packaging in order to more easily identify the linked drugs (prescription and over-the-counter).

Figure 3:
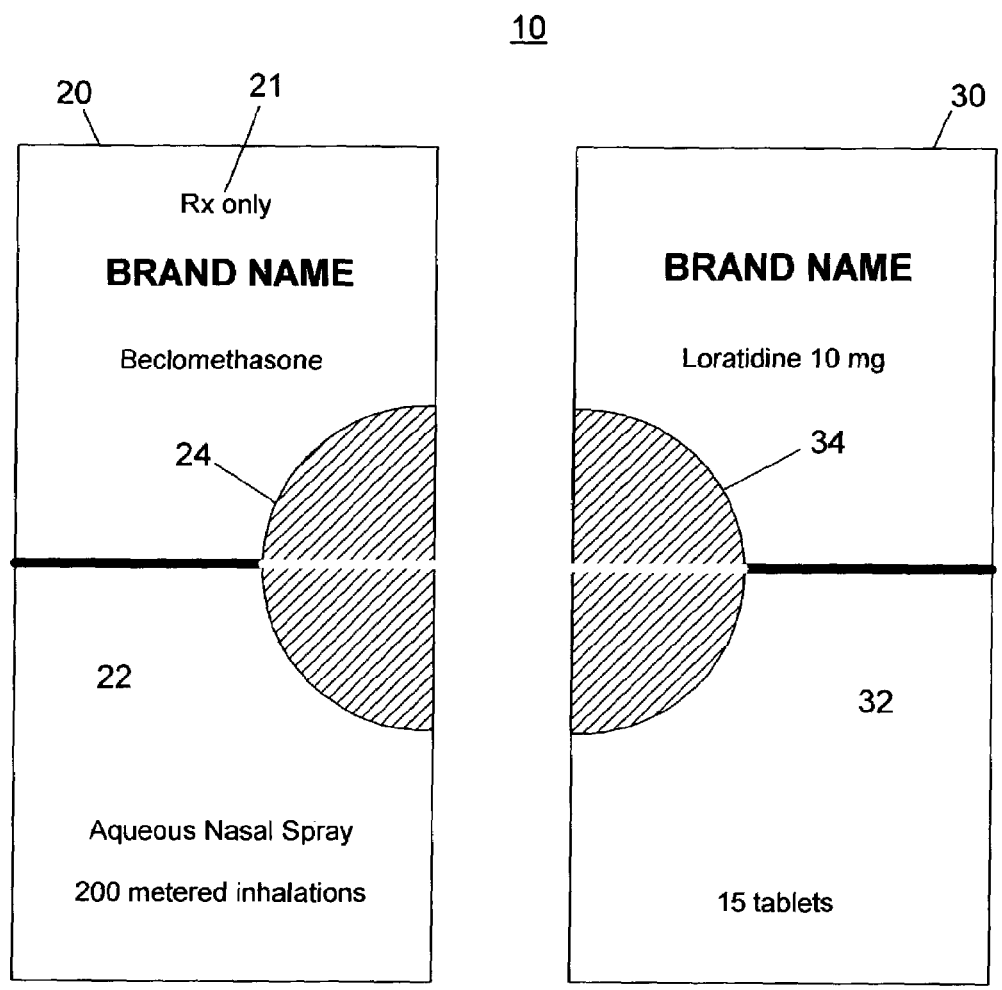
FIG. 3 is a front plan view of another embodiment of the present invention.

FIG. 3 illustrates another embodiment of drug packaging system 10 of the present invention. In this embodiment, prescription and over-the-counter drug dispensing containers 20 and 30, respectively, include mirror-image half-circle indicia 24 and 34 to indicate linkage or commonality. Half-circle indicia 24 on the prescription drug container 20 is intended to serve as a guide for procuring the over-the-counter drug that has a complementary half-circle indicia 34 on its container. In this example, only one indicia is used. However, it is considered that, in some instances, more than one indicia might be desired to enhance the certainty of guidance and confirmation.

In the example of FIG. 3, the prescription drug is the steroid nasal spray beclomethasone and the over-the-counter drug is the antihistamine loratidine. Individuals with allergic rhinitis are commonly treated with such a combination of medications by practitioners. In the past both have been prescription drugs. However, loratidine has recently been switched from prescription to over-the-counter status. It is presently sold alone and in formulation with 240 mg of pseudoephedrine. The current packaging used for the loratidine and the formulation with pseudoephedrine are quite similar.

Pseudoephedrine has known stimulatory and cardiovascular side effects that are of considerable risk in some patients despite its being an over-the-counter drug. Pseudoephedrine is contraindicated in narrow angle glaucoma and in patients receiving monamine oxidase (MAO) inhibitor therapy. It should be judiciously and sparingly used in hypertension, diabetes mellitus, ischemic heart disease, and renal disease, the latter because of reduced elimination of the drug. Like other sympathomimetic amines, it can produce central nervous system stimulation, convulsions, arrhythmias, and cardiovascular collapse. Notably, another over-the-counter sympathomimetic amine, phenylpropanolamine, has now been discontinued because of an increased incidence of stroke in individuals using it. A 240 mg dose of pseudoephedrine is a maximal daily dose and its administration assures persistent adrenergic stimulation.

Figure 4:
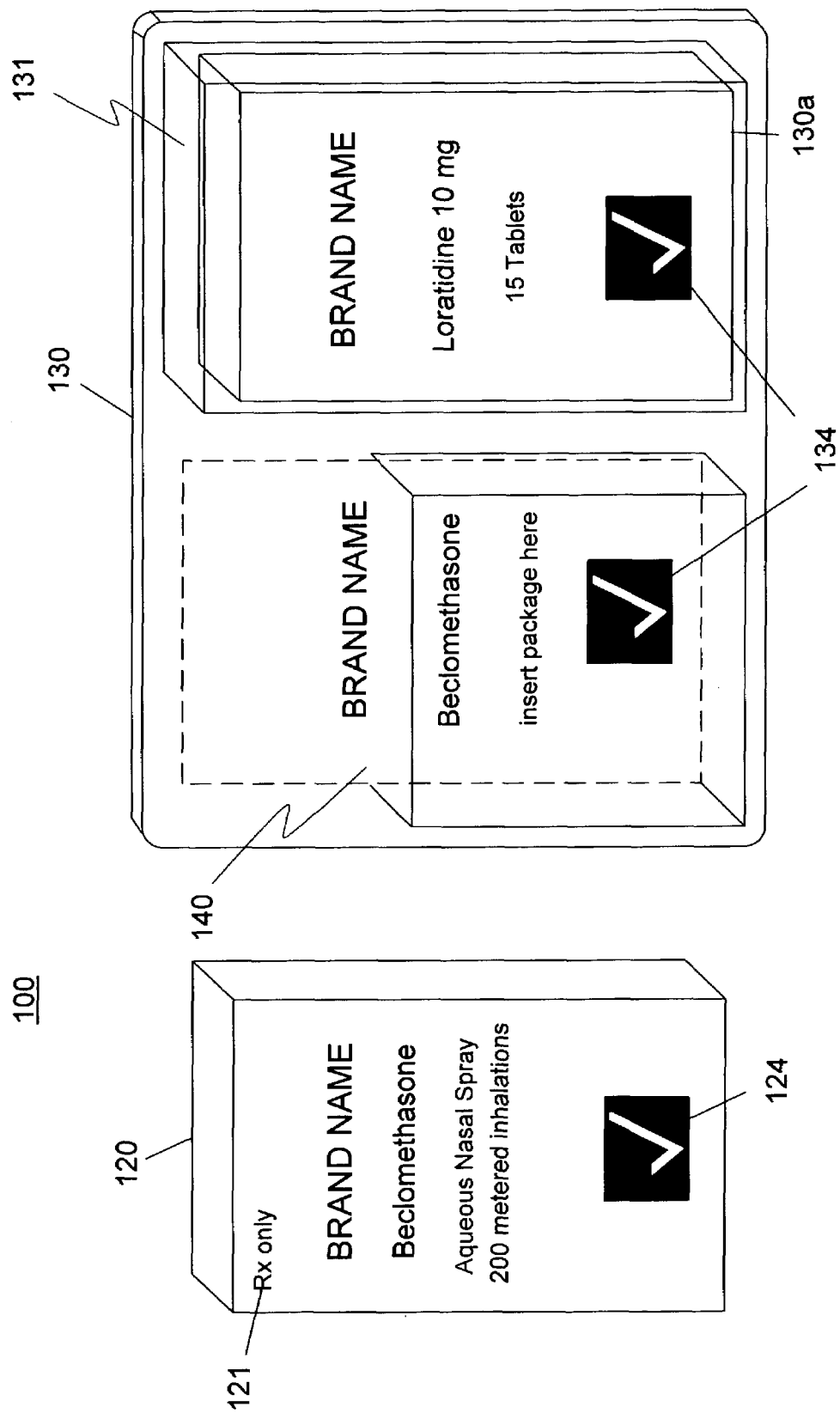
FIG. 4 is a perspective view of another embodiment of the present invention.

FIG. 4 illustrates yet another embodiment of the present invention using the example shown in FIG. 3. As previously discussed, if the wrong patient were to inadvertently procure and take 240 mg of pseudoephedrine daily serious health consequences may follow. The example in FIG. 4 shows how this embodiment can control the potential for "an accident waiting to happen." Drug packaging system 100 of this embodiment again includes a prescription drug package 120 and a linked over-the-counter drug package 130. Over-the-counter drug package 130 includes a location 140 for receiving prescription drug package 120. A blister type of packaging is depicted but a variety of configurations may be used. A requirement for a positive physical fit represents another form of indicia that might be utilized to avoid inadvertent procurement of unintended medication.

Prescription drug package 120 includes linking indicia 124 as well as prescription drug symbol 121 (Rx only). In this example, indicia 124 is a check design logo indicia. Drug package 130 includes a first location 131 for holding over-the-counter drug package 130a, which has linking indicia 134 that is identical to linking indicia 124, for the intended over-the-counter drug. Location 140 may also have words, symbols and other indicia that match or link to prescription drug package 120.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A medication dispensing system that allows a purchaser to identify on an over-the-counter shelf an over-the-counter drug intended by a caregiver to be procured with a prescription drug prescribed by the caregiver, said system comprising:
    a prescription drug dispensing container that contains a prescription drug;
    a separate over-the-counter drug dispensing container that contains an over-the-counter drug, said separate over-the-counter drug dispensing container being configured for displaying on said over-the-counter shelf and for procuring by the purchaser; and
    linking indicia displayed on said prescription drug dispensing container and said over-the-counter drug dispensing container wherein said linking indicia facilitates identification by the purchaser of said caregiver intended over-the-counter drug on said over-the-counter shelf to be procured with said prescription drug prescribed by the caregiver.

2. The system of claim 1 wherein said linking indicia is a name, a symbol, a graphic feature or a structural feature and combinations thereof.

3. An over-the-counter drug selection and guidance system that allows a purchaser to identify on an over-the-counter shelf an over-the-counter drug intended by a caregiver to be separately procured by the purchaser with a prescription drug prescribed by the caregiver, said system comprising:
    a prescription drug prepackaged by a manufacturer in a prescription drug dispensing container having guiding indica on at least one surface of said prescription drug dispensing container; and
    an over-the-counter drug separately prepackaged by a manufacturer in an over-the-counter drug dispensing container having a confirming indicia on at least one surface of said over-the-counter drug dispensing container wherein said confirming indicia links said over-the-counter drug to said guiding indicia of said prescription drug as said over-the-counter drug intended by the caregiver to be procured with said prescription drug, said separate over-the-counter drug dispensing container being configured for displaying on said over-the-counter shelf.

4. The selection and guidance system of claim 3 wherein said guiding indicia and said confirming indicia are a name, a symbol, a graphic feature or a structural feature and combinations thereof.

5. A method to guide the selection of an over-the-counter medication as an over-the-counter drug intended by a caregiver to be procured with a prescription drug prescribed by the caregiver, said method comprising:
    manufacturing a prescription drug in a prepackaged prescription drug dispensing container, said prescription drug container having guiding indicia thereon;
    manufacturing an over-the-counter drug in a separate prepackaged dispensing container, said container having a confirming indicia thereon wherein said confirming indicia links said over-the-counter drug to said guiding indicia on said prescription drug as said over-the-counter drug intended by the caregiver to be procured with said prescription drug, said separate over-the-counter drug dispensing container being configured for displaying on said over-the-counter shelf.

6. The method of claim 5 further comprising using a name, a symbol, a graphic feature or a structural feature and combinations thereof as said guiding and confirming indicia.

7. A method to reduce error in the procurement of an over-the-counter drug by a patient when said over-the-counter drug is advised for use together with a prescription drug, said method comprising:
    prescribing a prescription drug in a prepackaged prescription drug dispensing container that has a linking indicia disposed thereon;
    recommending an over-the-counter drug in a package having indicia disposed thereon that links said indicia to said linking indicia of said prescription drug and identifies said over-the-counter drug as said over-the-counter drug advised for use together with said prescription drug; and
    instructing the patient to use said linking indicia to select said over-the-counter drug from said over-the-counter shelf as a caregiver-intended treatment component to said prescription drug.

8. A pharmaceutical dispensing method that allows a purchaser to identify on an over-the-counter shelf an over-the-counter drug intended by a caregiver to be procured with a prescription drug prescribed by the caregiver, said method comprising:
    stocking a prescription drug for sale in a prescription drug packaging that contains guiding indicia;
    stocking on said over-the-counter shelf said over-the-counter drug for sale in packaging configured for displaying on said over-the-counter shelf, said over-the-counter drug packaging containing confirmatory indicia wherein said confirmatory indicia links said confirmatory indicia to said guiding indicia on said prescription drug and identifies to the purchaser said over-the-counter drug as said over-the-counter drug intended by said caregiver to be separately procured by the purchaser; and
    dispensing said prescription drug to the purchaser having a prescription for said prescription drug.

9. A medication dispensing system that allows a purchaser to identify an over-the-counter drug intended by a caregiver to be procured with a prescription drug prescribed by the caregiver, said system comprising:

a prescription drug dispensing means that contains a prescription drug;

separate over-the-counter drug dispensing means that contains an over-the-counter drug, said separate over-the-counter drug dispensing means being configured for displaying on an over-the-counter shelf; and linking means on said prescription drug dispensing means and said over-the-counter drug dispensing means wherein said linking means facilitates identification by the purchaser of the caregiver intended over-the-counter drug to be procured with said prescription drug prescribed by said caregiver.

10. The system of claim 9 wherein said linking means is a name, a symbol, a graphic feature or a structural feature and combinations thereof.

* * * * *